(12) United States Patent
O'Donnell et al.

(10) Patent No.: US 9,149,608 B2
(45) Date of Patent: Oct. 6, 2015

(54) HANDLE HAVING HUB WITH ROTATING INFUSION SIDEPORT

(71) Applicants: Joseph A. O'Donnell, Escondido, CA (US); Steven T. Onishi, Cupertino, CA (US); Damian Muldoon, Loughrea (IE)

(72) Inventors: Joseph A. O'Donnell, Escondido, CA (US); Steven T. Onishi, Cupertino, CA (US); Damian Muldoon, Loughrea (IE)

(73) Assignee: Boston Scientific Scimed Inc., Maple Grove, MN (US)

( * ) Notice: Subject to any disclaimer, the term of this patent is extended or adjusted under 35 U.S.C. 154(b) by 323 days.

(21) Appl. No.: 13/722,987

(22) Filed: Dec. 20, 2012

(65) Prior Publication Data

US 2013/0165857 A1    Jun. 27, 2013

Related U.S. Application Data

(60) Provisional application No. 61/579,097, filed on Dec. 22, 2011.

(51) Int. Cl.
*A61M 31/00* (2006.01)
*A61M 37/00* (2006.01)
(Continued)

(52) U.S. Cl.
CPC ....... *A61M 25/0147* (2013.01); *A61M 25/0097* (2013.01); *A61M 25/0136* (2013.01);
(Continued)

(58) Field of Classification Search
CPC ............... A61B 1/00066; A61B 1/015; A61B 2017/003; A61B 18/1492; A61B 1/0052; A61M 25/0097; A61M 25/0136; A61M 25/0147; A61M 39/06; A61M 39/1055; A61M 25/0144; A61M 2025/015; A61M 2025/0681; A61M 25/0105
USPC ........................................ 604/95.04
See application file for complete search history.

(56) References Cited

U.S. PATENT DOCUMENTS 5,370,624 A    12/1994    Edwards et al.
6,245,045 B1    6/2001    Stratienko
(Continued)

FOREIGN PATENT DOCUMENTS

EP    0566426 A1    10/1993
EP    1050316 B1    12/2003
(Continued)

OTHER PUBLICATIONS

International Search Report and Written Opinion issued in PCT/US2012/071058, mailed Feb. 28, 2013, 16 pages.
(Continued)

*Primary Examiner* — Jason Flick
(74) *Attorney, Agent, or Firm* — Faegre Baker Daniels LLP (57) ABSTRACT

An introducer sheath assembly comprises a tubular sheath member having a deflectable distal end portion and a sheath member lumen, a handle assembly including a steering mechanism for deflecting the distal end portion of the sheath member, and a hemostasis valve assembly. The hemostasis valve assembly includes a side port member configured to be connected to a fluid source for introducing fluid into the sheath member lumen. The side port member is axially rotatable relative to the handle assembly and the sheath member such that the side port member can remain rotationally fixed relative to the fluid source as the handle assembly and the sheath member are rotated relative to the fluid source. The side port member may also be made transparent to allow for easy visualization of air bubbles, and is also configured to allow for evacuation of any visualized air bubbles.

16 Claims, 3 Drawing Sheets

(51) Int. Cl.
*A61M 25/00* (2006.01)
*A61M 25/01* (2006.01)
*A61M 39/06* (2006.01)
*A61M 39/10* (2006.01)
*A61M 39/22* (2006.01)
*A61B 1/00* (2006.01)
*A61B 1/015* (2006.01)

(52) U.S. Cl.
CPC ........... *A61M39/06* (2013.01); *A61M 39/0606* (2013.01); *A61M 39/1055* (2013.01); *A61M 39/22* (2013.01); *A61B 1/00066* (2013.01); *A61B 1/015* (2013.01); *A61M 2039/0633* (2013.01); *A61M 2039/229* (2013.01)

(56) References Cited

U.S. PATENT DOCUMENTS

| | | |
|---|---|---|
| 2005/0277874 A1 | 12/2005 | Selkee |
| 2006/0142699 A1 | 6/2006 | Lampropoulos |
| 2008/0039918 A1 | 2/2008 | Falwell et al. |
| 2009/0281524 A1 | 11/2009 | Scheibe et al. |
| 2013/0184642 A1 | 7/2013 | O'Donnell et al. |
| 2013/0331692 A1* | 12/2013 | Mouri ................... 600/435 |

FOREIGN PATENT DOCUMENTS

| | | | |
|---|---|---|---|
| EP | 1607118 B1 | 12/2005 | |
| EP | 2116272 B1 | 11/2009 | |
| EP | 2204208 A2 | 7/2010 | |
| EP | 2438954 A1 * | 4/2012 | ............ A61M 25/01 |
| EP | 2465568 A1 | 6/2012 | |
| WO | WO9841275 A1 | 9/1998 | |
| WO | WO2012114633 A1 | 8/2012 | |

OTHER PUBLICATIONS

International Search Report and Written Opinion issued in PCT/US2012/071084, mailed Mar. 8, 2013, 19 pages.

* cited by examiner

HANDLE HAVING HUB WITH ROTATING INFUSION SIDEPORT

CROSS-REFERENCE TO RELATED APPLICATION

This application claims priority to U.S. Provisional Application 61/579,097, filed Dec. 22, 2011, which is herein incorporated by reference in its entirety.

TECHNICAL FIELD

The present invention relates to medical introducer sheaths for introducing medical devices into the body. In particular, the present invention relates to deflectable introducer sheaths and associated hemostasis valves.

BACKGROUND

Introducer sheaths are important instruments for use in medical diagnostic and therapeutic procedures. In particular, introducer sheaths can be used by a clinician to access target areas of the patient's anatomy, e.g., the patient's cardiovascular system, and also allow for diagnostic and/or therapeutic payloads (such as ablation catheters) to be inserted into these target areas. Introducer sheaths often include hemostasis valves that permit introduction of the desired payloads but at the same time inhibit undesired fluid loss from the introducer sheath.

SUMMARY

In Example 1, the present invention is an introducer sheath assembly comprising a tubular sheath member, and a hemostasis valve assembly. The tubular sheath member has a proximal end portion including a proximal end, a distal end portion terminating in a distal tip, and an internal sheath lumen extending through the proximal and distal end portions of the sheath member. The hemostasis valve assembly includes a distal end portion coupled to the proximal end of the sheath member, a proximal opening generally aligned with the sheath lumen to permit introduction of an instrument therethrough, a seal member positioned distal to the proximal opening to inhibit fluid leakage through the proximal opening, and a side port member between the seal member and the distal end portion of the hemostasis valve assembly. The side port member includes a side wall having an inner surface defining an interior chamber in fluid communication with the sheath lumen, a side port fitting extending laterally from the sidewall and including a side port lumen extending through the side wall in fluid communication with the interior chamber. The side port member is configured to be axially rotatable relative to the sheath member and the handle assembly.

In Example 2, the introducer sheath assembly of Example 1, wherein the hemostasis valve assembly further includes a tubular body member including an outer surface and an inner surface defining a longitudinal channel, a portion of the body member disposed within the interior chamber of the side port member and including a lateral through hole extending through the outer and inner surfaces and fluidly coupling the longitudinal channel with the side port lumen and the interior chamber of the side port member.

In Example 3, the introducer sheath assembly of either of Examples 1 or 2, wherein one or both of the side port member and the body member are made of a substantially transparent material.

In Example 4, the introducer sheath assembly of either of Examples 2 or 3, wherein the side port member is axially rotatable relative to the body member.

In Example 5, the introducer sheath assembly of any of Examples 2-4, wherein the through hole in the body member is located at substantially the same axial position as the side port lumen such that the through hole, the side port lumen, the interior chamber of the side port member and the longitudinal channel of the body member remain in fluid communication as the side port member is rotated relative to the body member.

In Example 6, the introducer sheath assembly of any of Examples 2-5, wherein the outer surface of the body member further includes a circumferential recess extending radially inwardly around the body member, and wherein the through hole is located within the circumferential recess.

In Example 7, the introducer sheath assembly of any of Examples 2-6, wherein the outer surface of the body member further includes a first circumferential groove located proximal to the circumferential recess, and a second circumferential groove located distal to the circumferential recess, and wherein the hemostasis valve assembly further includes a first seal ring retained within the first circumferential groove and a second seal ring retained within the second circumferential groove, the first and second seal rings configured to seal against an interior surface of the side port member side wall.

In Example 8, the introducer sheath assembly of any of Examples 2-7, wherein the side port member includes a proximal end face and a distal end face.

In Example 9, the introducer sheath assembly of any of Examples 2-8, wherein the distal end portion includes a proximal face having an annular groove, and a distal end connected to the proximal end of the sheath member, and wherein the body member includes a distal annular lip configured to be received within the annular groove of the distal fitting to secure the body member to the distal fitting.

In Example 10, the introducer sheath assembly of any of Examples 2-9, wherein the body member further includes a proximal end portion, and wherein the hemostasis valve assembly further includes an end cap secured to the proximal end portion of the body member, the end cap including the proximal opening of the hemostasis valve assembly.

In Example 11, the introducer sheath assembly of any of Examples 2-10, wherein the proximal end portion of the body member further includes a radial flange abutting the proximal face of the side port member, and a circumferential notch located proximal to the radial flange, and wherein the end cap includes an inwardly extending circumferential tab that engages the circumferential notch to secure the end cap to the body member.

In Example 12, the introducer sheath assembly of either of Examples 10-11, wherein the seal member is retained between the proximal end portion of the body member and the end cap, and wherein the proximal end portion of the body member includes an annular groove oriented toward the end cap, and wherein the seal member includes a proximal face and a distal face, and an annular lip extending axially from the distal face configured to be received in the annular groove of the body member.

In Example 13, the introducer sheath assembly of any of Examples 1-12, further comprising a handle assembly coupled to the sheath member, and first and second pull wires connected to the sheath member proximate the distal end thereof and extending into and connected to the handle assembly, and wherein the handle assembly is operable by a user to manipulate the pull wires to affect a shape of the sheath member proximate the distal end thereof.

In Example 14, the present invention is a deflectable introducer sheath assembly comprising a tubular sheath member, a handle assembly and a hemostasis valve assembly. The tubular sheath member has a proximal end portion including a proximal end, a distal end portion terminating in a distal tip, and an internal sheath lumen extending through the proximal and distal end portions of the sheath member. The handle assembly is coupled to the proximal end portion of the sheath member. At least a first pull wire is connected to the sheath member proximate the distal tip thereof and extends into and is coupled to the handle assembly. The handle assembly is operable by a user to manipulate the first pull wire to affect a shape of the distal end portion of the sheath member. The hemostasis valve assembly is coupled to the proximal end of the sheath member and is configured to permit introduction of an instrument into the sheath lumen while inhibiting fluid leakage from the introducer sheath assembly. The hemostasis valve assembly includes a side port member including a side port fitting having a side port lumen in fluid communication with the sheath lumen. The side port member is axially rotatable relative to the sheath member and the handle assembly.

In Example 15, the introducer sheath assembly of Example 14, wherein the side port member is tubular and includes a sidewall having an inner surface defining an interior chamber in fluid communication with the sheath lumen, and wherein the side port lumen extends through the side wall.

In Example 16, the introducer sheath assembly of either of Examples 14 or 15, wherein the hemostasis valve assembly further includes a tubular body member including an outer surface and an inner surface defining a longitudinal channel, a portion of the body member disposed within the interior chamber of the side port member and including a lateral through hole extending through the outer and inner surfaces and fluidly coupling the longitudinal channel with the side port lumen and the interior chamber of the side port member.

In Example 17, the introducer sheath assembly of Example 16, wherein one or both of the side wall of the side port member and the body member are made of a substantially transparent material.

In Example 18, the present invention is an introducer assembly comprising a tubular sheath member, a handle assembly, and a hemostasis valve assembly. The tubular sheath member can have a proximal end portion including a proximal end, a distal end portion terminating in a distal tip, and an internal sheath lumen extending through the proximal and distal end portions of the sheath member. The handle assembly can be coupled to the proximal end portion of the sheath member. The hemostasis valve assembly can be coupled to the proximal end of the sheath member and configured to permit introduction of an instrument into the sheath lumen while inhibiting fluid leakage from the introducer sheath assembly, the hemostasis valve assembly including a side port member including a side port fitting having a side port lumen in fluid communication with the sheath lumen. The side port member is axially rotatable relative to the sheath member and the handle assembly.

In Example 19, the introducer assembly of Example 18, wherein the hemostasis valve assembly further includes a tubular body member including an outer surface and an inner surface defining a longitudinal channel, a portion of the body member disposed within the interior chamber of the side port member and including a lateral through hole extending through the outer and inner surfaces and fluidly coupling the longitudinal channel with the side port lumen and the interior chamber of the side port member.

In Example 20, the introducer assembly of Example 19, wherein the through hole in the body member is located at substantially the same axial position as the side port lumen such that the through hole, the side port lumen, the interior chamber of the side port member and the longitudinal channel of the body member remain in fluid communication as the side port member is rotated relative to the body member.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

While the invention is amenable to various modifications and alternative forms, specific embodiments have been shown by way of example in the drawings and are described in detail below. The intention, however, is not to limit the invention to the particular embodiments described. On the contrary, the invention is intended to cover all modifications, equivalents, and alternatives falling within the scope of the invention as defined by the appended claims.

DETAILED DESCRIPTION

Figure 1A:
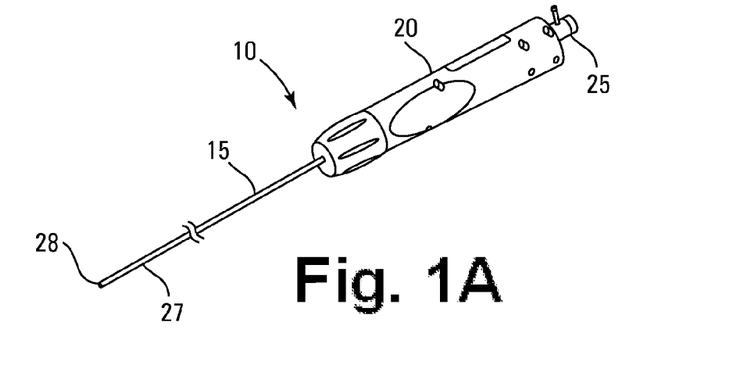
FIG. 1A is an isometric view of an exemplary introducer sheath assembly according to one embodiment of the present invention.

FIG. 1A is a plan view of an exemplary introducer sheath assembly 10 according to one embodiment of the present invention. The introducer sheath assembly 10 is configured for use in a broad range of medical procedures requiring the introduction of a payload into the body. For example, in various embodiments, the introducer sheath assembly 10 can be used to introduce therapeutic and/or diagnostic electrophysiology catheters, e.g., ablation and/or mapping catheters, into a heart chamber. In other embodiments, the introducer sheath assembly 10 can be used to deliver implantable devices, e.g., pacing leads, to a heart chamber or to a coronary vein. In short, the present invention is not limited to any particular clinical use.

As shown in FIG. 1A, the introducer sheath assembly 10 includes a sheath member 15, a handle assembly 20 and a hemostasis valve assembly 25. In the illustrated embodiment, the handle assembly 20 is coupled to the sheath member 15 distal to the hemostasis valve assembly 25, which occupies the proximal-most position on the introducer sheath assembly 10. As will be explained in further detail below, the sheath member 15 includes a lumen extending longitudinally therethrough sized to allow introduction of a payload into the introducer sheath assembly 10 and out the distal end of the sheath member 15. Additionally, in various embodiments, the sheath member 15 includes a deflectable distal end portion 27 that can assume a variety of different shapes for navigating the patient anatomy, and as shown in FIG. 1A, terminates in a distal tip 28.

In general, the handle assembly 20 is configured to allow a clinician to manipulate and control the introducer sheath assembly 10, and in particular, includes a mechanism for altering the shape of the distal end portion 27 of the sheath member 15 to assist in navigating the patient anatomy, as explained in further detail below. The hemostasis valve assembly 25 is configured to allow introduction of a payload into the lumen of the sheath member 15 while at the same time inhibiting unintended leakage of fluid from the sheath member 15 into the operating environment and/or aspiration of air into the sheath member 15 lumen. Additionally, as explained in further detail below, the hemostasis valve assembly 25 is configured to include a portion that is axially rotatable (i.e., rotatable about the theoretical longitudinal axis of the introducer sheath assembly 10) relative to the handle assembly 20 and the sheath member 15 to aid in the operability and ease of use of the introducer sheath assembly 10.

Figure 1B:
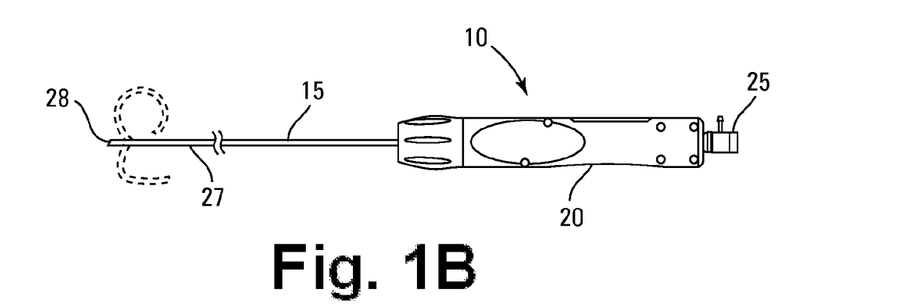
FIG. 1B is a plan view of the introducer sheath assembly of FIG. 1A illustrating the deflectability of the sheath according to one embodiment of the present invention.

In the various embodiments illustrated, the introducer sheath assembly 10 is a deflectable or steerable introducer sheath, in that the shape or profile of at least the distal end portion 27 of the sheath member 15 can be altered, i.e., by manipulation of a steering mechanism in the handle assembly 20, to facilitate navigation of the patient anatomy. FIG. 1B is a plan view of the introducer sheath assembly 10 illustrating the deflectability of the sheath member 15. As indicated by the phantom lines in FIG. 1B, the distal end portion 27 can be deflected relative to its "straight" or undeflected state shown in FIG. 1A.

Deflection of the distal end portion 27 of the sheath member 15 can be effectuated by the inclusion of pull wires (not shown) extending within the sheath member 15 and fixedly connected to the sheath member 15 within the distal end portion 27 at one end, and to the handle assembly 20 at the other end. In various embodiments, these pull wires are each secured to the sheath member 15 near its distal tip 28 (e.g., by attaching the pull wires to an anchor member incorporated into the sheath member 15) such that the distal ends of the pull wires are fixed relative to the sheath member 15. Accordingly, by selectively applying tension to the respective pull wires (e.g., via the steering mechanism incorporated into the handle assembly 20), the distal end portion 27 is deflected. It is noted that the embodiments of the present invention are not in any way limited by the technique by which the pull wires are routed through the sheath member 15, secured to the distal end portion 27 thereof, or whether the sheath member 15 is even deflectable or present.

In addition, except as otherwise discussed herein, the particular construction of the sheath member 15 in the various embodiments is not critical, and thus will not be discussed in great detail. In short, any number of construction details can be utilized for the sheath member 15 within the scope of the embodiments of the present invention. For example, the sheath member can have a single or multiple layer polymer construction, and may or may not include one or more reinforcing elements (e.g., braids, coils, wires, etc.) to enhance the mechanical characteristics, e.g., stiffness, torquability and the like, of the sheath member 15. In one embodiment, the sheath member 15 includes an outer layer of a biocompatible polymer such as a polyether block amide, an inner layer of a lubricious polymeric material such as polytetrafluoroethylene (PTFE), ethylene tetrafluoroethylene (ETFE), silicone, and the like, with a stainless steel braid and/or stainless steel wire coil embedded between the outer and inner polymer layers. In various embodiments, the durometer of the polymeric materials making up the outer and/or inner layers may be varied along the length of the sheath member 15 to further tailor the mechanical characteristics to the needs of the end user. Again, unless specifically discussed herein, the construction of the sheath member 15 is in no way limited to any particular construction.

Figure 2:
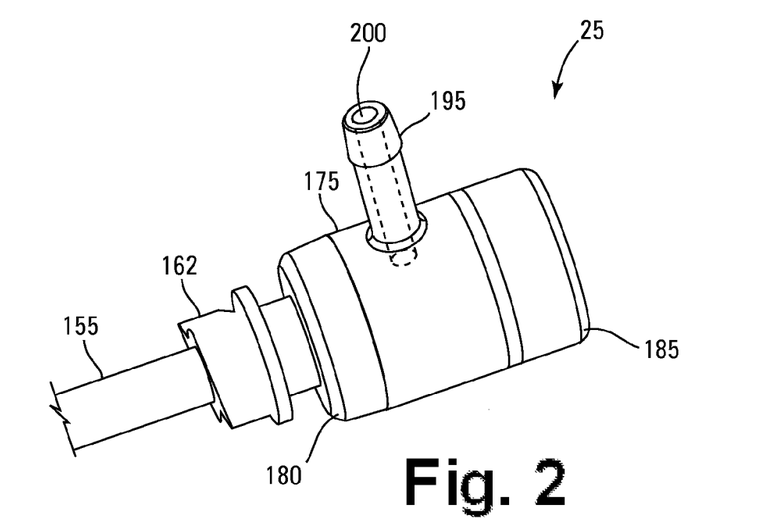
FIG. 2 is a partial isometric view of the introducer sheath assembly of FIG. 1A showing the attachment of a hemostasis valve assembly to the sheath member according to one embodiment of the present invention.
Figure 3:
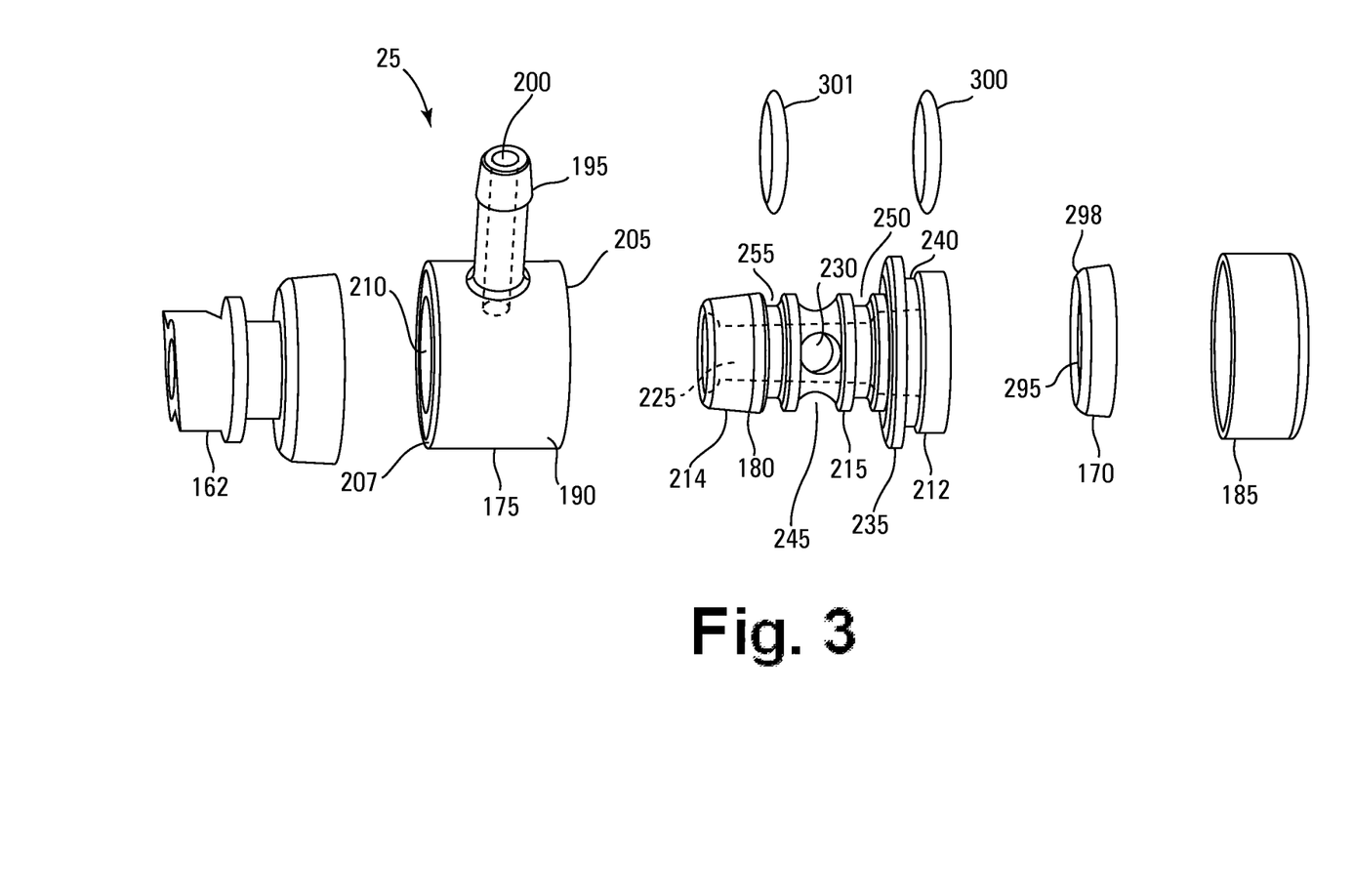
FIG. 3 is an exploded view of the hemostasis valve assembly of the introducer sheath assembly of FIG. 1A according to one embodiment of the present invention.
Figure 4:
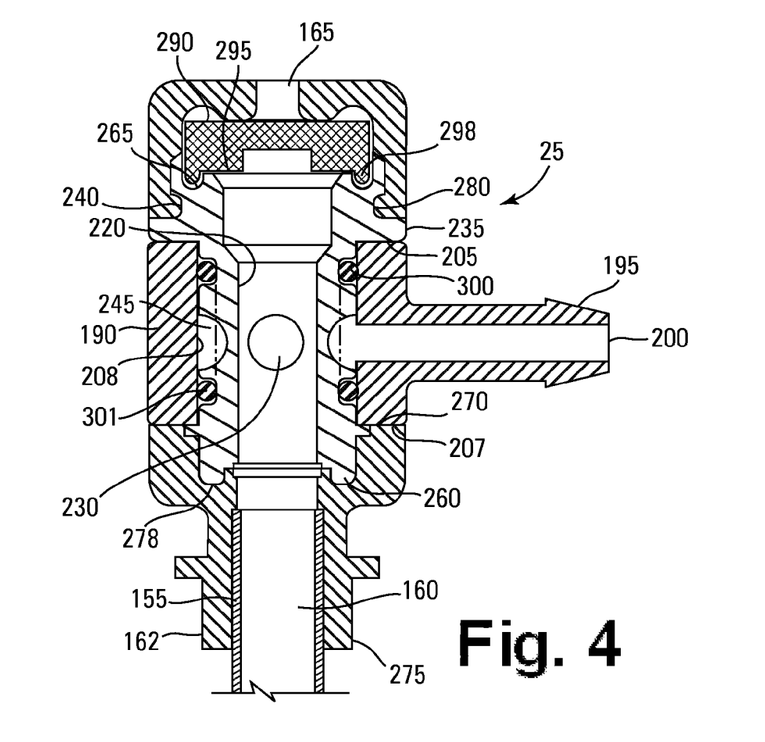
FIG. 4 is a cross-sectional elevation view of the hemostasis valve assembly of the introducer sheath assembly of FIG. 1A according to one embodiment of the present invention.

The construction of the hemostasis valve assembly 25 will now be discussed by reference to FIGS. 2-4. FIG. 2 is a partial isometric view of the introducer sheath assembly 10 showing the attachment of the hemostasis valve assembly 25 to the proximal end of the sheath member 15 according to one embodiment of the present invention. FIG. 3 is an exploded view of the hemostasis valve assembly 25, and FIG. 4 is a cross-sectional elevation view of the hemostasis valve assembly 25 and the proximal end of the sheath member 15.

As shown, the sheath member 15 includes a proximal end 155 and an internal lumen 160, and the hemostasis valve assembly 25 includes a distal end fitting 162 coupled to the proximal end 155 of the sheath member. The hemostasis valve assembly 25 further includes a proximal opening 165 generally aligned with the sheath lumen 160 to permit introduction of an instrument therethrough.

As further shown, the hemostasis valve assembly 25 further includes a seal member 170, a side port member 175, a body member 180 and an end cap 185. The seal member 170 is positioned distal to the proximal opening 165 to inhibit fluid leakage through the proximal opening 165, and the side port member 175 is positioned between the seal member 170 and the distal end fitting 162 of the hemostasis valve assembly 25.

As further shown, the side port member 175 includes a side wall 190, a side port fitting 195 including a side port lumen 200, a proximal end face 205 and an opposite distal end face 207. In the illustrated embodiment, the side port fitting 195 extends laterally from the side wall 190, and the side wall 190 extends between the proximal end face 205 and the distal end face 207 and has an inner surface 208 defining an interior chamber 210 that, in the assembled hemostasis valve assembly 25, is in fluid communication with the sheath lumen 160.

As also shown, the body member 180 includes a proximal end portion 212, an opposite distal end portion 214, an outer surface 215 and an inner surface 220. As shown, the inner surface 220 defines an interior longitudinal channel 225. As further shown, the body member 180 has at least one lateral through hole 230 extending from the outer surface 215 to the inner surface 220. In various embodiments, the body member 180 has a plurality of through holes 230, which may be generally spaced about the longitudinal axis of the body member 180. As can be seen in FIG. 4, in the assembled hemostasis valve assembly 25, the body member 180 is partially disposed within the interior chamber 210 of the side port member 175 with the through hole 230 aligned longitudinally with the side port fitting 195.

As further shown, the body member 180 includes a radial flange 235 in the proximal end portion 212, and a circumferential notch 240 located a circumferential notch located proximal to the radial flange 235. In the illustrated embodiment, in the assembled hemostasis valve assembly 25, the radial flange 235 abuts the proximal end face 205 of the side port member 175. Additionally, the outer surface 215 of the body member 180 further includes a circumferential recess 245 extending radially inwardly and circumferentially around the body member 180, a proximal circumferential groove 250 located proximally of the circumferential recess 245, and a distal circumferential groove 255 located distally of the circumferential recess 245. As further shown, the through hole 230 is located within the circumferential recess 245. Additionally, in the illustrated embodiment, the body member 180 further includes a distal annular lip 260 and a proximal annular groove 265.

As further shown, the distal end fitting 162 includes a proximal face 270, a distal end 275 and an annular groove 278 in the proximal face 270. As can be seen in FIG. 4, when the hemostasis valve assembly 25 is assembled, the body member 180 mates with the distal end fitting 162, with the distal annular lip 260 of the body member 180 received in the annular groove 278 in the proximal face 270 of the distal end fitting 162. Thus, in the illustrated embodiment, the distal fitting 162 and the body member 180 are separate elements coupled together in the assembled hemostasis valve assembly 25 such as is shown in FIG. 4. In other embodiments, however, the distal fitting 162 and the body member 180 can be formed as an integral piece. In the illustrated embodiment, the distal end fitting 162 is fixedly attached to the sheath member 15, which attachment can be accomplished by any suitable attachment technique, e.g., ultrasonically welding, adhesives, and the like. In various other embodiments, the distal end fitting 162 can be Luer lock fitting or comparable structure such that it can be releasably coupled to a hub on the sheath member 15 or the handle assembly 20.

As further shown, the end cap 185 includes a circumferential tab 280 that extends radially inwardly of the outer periphery of the end cap 185. As can be seen in FIG. 4, in the assembled hemostasis valve assembly 25, the circumferential tab 280 engages the circumferential notch 240 in the body member 180 to secure the end cap 185 to the body member 180. In various embodiments, the engagement of the end cap 185 to the body member 180 can be by a snap fit or similar type of coupling arrangement. In various other embodiments, the end cap 185 may be joined to the body member 180 by other means, e.g., an interference fit, a threaded connection, and the like. In various embodiments, the end cap 185 may be permanently joined to the body member 180, e.g., by the use of a medical grade adhesive or an ultrasonic weld.

In the illustrated embodiment, the seal member 170 includes a proximal face 290, a distal face 295 and an annular lip 298 extending axially from the distal face 290. As shown in FIG. 4, when assembled, the annular lip 298 is received in the proximal annular groove 265 of the body member 180, which is oriented toward the seal member 170. This mating arrangement between the annular lip 298 and the proximal annular groove 265 advantageously assists in aligning and retaining the seal member 170 between the body member 180 and the end cap 195. In various embodiments, however, the annular lip 298 is omitted, and the seal member 170 is merely sandwiched between the body member 180 and the end cap 185. In various embodiments, the seal member 170 also includes a feature, e.g., a slit, aperture, or weakened area, that facilitates passage of a medical instrument or payload longitudinally across the seal member 170. It is emphasized, however, that the particular configuration of the seal member 170 and the end cap 185 are not critical to any of the various embodiments of the present invention.

As further shown, the hemostasis valve assembly 25 includes seal rings 300, 301 retained, respectively, in the proximal circumferential groove 250 and the distal circumferential groove 255, respectively, of the body member 180. The seal rings 300, 301, which in the illustrated embodiment are in the form of O-rings, are configured to seal against the inner surface of the side port member side wall 190 in the assembled hemostasis valve assembly 25.

Thus, as can be seen, for example, in FIG. 4, when the hemostasis valve assembly 25 is assembled, the body member 180 is partially inserted into the interior chamber 210 of the side port member 175 and is coupled to the distal end fitting 162 with the distal annular lip 260 of the body member 180 received in and engaged with the annular groove 278 in the proximal face 270 of the distal end fitting 162. Additionally, the radial flange 235 of the body member 180 abuts the proximal end face 205 of the side port member 175, and the distal end face 207 of the side port member 175 abuts the proximal face 270 of the distal end fitting 162, thus fixing the longitudinal position of the side port member 175 between the distal end fitting 162 and the radial flange 235 of the body member 180. As further shown, the through hole 230 in the body member 180 is located at substantially the same axial position as the side port fitting 195 and the side port lumen 200 such that the through hole 230, the side port lumen 200, the interior chamber 210 of the side port member 175 and the longitudinal channel 225 of the body member 180 are in fluid communication with one another and also with the sheath lumen 160.

In various embodiments, the side port member 175 and the body member 180 are made of a substantially transparent material. The transparency of the side port member 175 and the body member 180 advantageously allows for easy visualization of any air bubbles that may be introduced during the use of the introducer sheath assembly 10. In such embodiments, any air bubbles can be evacuated using a syringe fluidly coupled to the side port lumen 200, e.g., via a 3 way stopcock.

In various embodiments, the configuration of the hemostasis valve assembly 25 is such that the side port member 175 is axially rotatable (i.e., is rotatable about an imaginary axis extending longitudinally through the hemostasis valve assembly 25 as well as the handle assembly 20 and the sheath member 15) relative to the body member 180, the distal end fitting 162 and the end cap 185. Additionally, the side port member 175 is also axially rotatable relative to the handle assembly 20 and the sheath member 15. As can be seen in FIG. 4, the circumferential recess 245 in the body member outer surface 215 forms a circumferential fluid cavity between the outer surface 215 and the inner surface 208 of the side wall 190 of the side port member 175. Because the through hole 230 of the body member 180 is located within the circumferential recess 245, this cavity operates to maintain fluid communication between the side port lumen 200, the longitudinal channel 225 of the body member 180 and, consequently, the sheath lumen 160 after and during rotation of the side port member 175 relative to the body member 180, even when the through hole 230 is not radially aligned with the side port lumen 200 (i.e., as a result of this relative rotation of the side port member 175 and the body member 180). In the illustrated embodiment, the seal rings 300, 301 operate to inhibit leakage of fluid from between the body member 180 and the side port member 175.

This relative axial rotatability greatly increases the ease of use of the introducer sheath assembly 10. For example, in various clinical procedures, fluid, e.g., saline, drugs and the like may be introduced through the side port lumen 200 and into the sheath lumen 160. In such a case, tubing is connected to the side port fitting 195 and also to a fluid source such as a syringe, and IV bag, and the like. At the same time, the clinical procedure often requires rotation of the handle assembly 20 by the clinician, which rotation would otherwise be inhibited if the side port member 175 was not rotatable relative to the handle assembly 20. However, in various embodiments of the introducer sheath assembly 10, the handle assembly 20 can be rotated relative to the fluid source while the side port member 175, which is connected to the fluid source via the side port fitting 195, can remain in the same rotational position relative to the fluid source. The rotatability also enhances the ease in which an air bubble is positioned in close proximity to the opening of side port lumen 200 so that the bubble can be removed through tubing coupled to a syringe. For example, by rotating the side port member 175, air bubbles inadvertently introduced into the hemostasis valve 25 can be caused to migrate toward the side port lumen 200 and thereafter removed.

In various embodiments, the shape of the side port member 175 is not uniformly cylindrical. For example, in various embodiments, the side port member 175 is configured such that the diameter of the interior chamber 210, particularly the portion between the seal rings 300, 301 is increased compared to the illustrated embodiment. As such, the volume of the space between the inner surface 208 of the side port member 175 and the outer surface 215 of the body member 180 is increased. This increase in volume will allow aberrant air bubbles to float to the highest point in the chamber 210, thus further facilitating removal of the air bubbles.

Although the hemostasis valve assembly 25 is illustrated being used in conjunction with the steerable or deflectable introducer sheath assembly 10, in various embodiments, the hemostasis valve assembly 25 can also be used with so-called fixed shape introducer sheaths that do not include any pull wires, steering mechanisms or similar structures to alter the distal shape of the catheters.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

We claim:

1. An introducer sheath assembly comprising:
   a tubular sheath member having a proximal end portion including a proximal end, a distal end portion terminating in a distal tip, and an internal sheath lumen extending through the proximal and distal end portions of the sheath member;
   a distal end fitting including a proximal face having an annular groove, and a distal end connected to the proximal end of the sheath member; and
   a body member including a distal annular lip configured to be received within the annular groove of the distal fitting to secure the body member to the distal fitting; and
   a hemostasis valve assembly including a distal end portion coupled to the proximal end of the sheath member, a proximal opening generally aligned with the sheath lumen to permit introduction of an instrument therethrough, a seal member positioned distal to the proximal opening to inhibit fluid leakage through the proximal opening, and a side port member between the seal member and the distal end portion of the hemostasis valve assembly, the side port member including:
   a side wall having an inner surface defining an interior chamber in fluid communication with the sheath lumen; and
   a side port fitting extending laterally from the sidewall and including a side port lumen extending through the side wall in fluid communication with the interior chamber,
   wherein the side port member is configured to be axially rotatable relative to the sheath member and a handle assembly.

2. The introducer sheath assembly of claim 1, wherein the body member includes an outer surface and an inner surface defining a longitudinal channel, a portion of the body member disposed within the interior chamber of the side port member and including a lateral through hole extending through the outer and inner surfaces and fluidly coupling the longitudinal channel with the side port lumen and the interior chamber of the side port member.

3. The introducer sheath assembly of claim 2, wherein one or both of the side port member and the body member are made of a substantially transparent material.

4. The introducer sheath assembly of claim 2, wherein the side port member is axially rotatable relative to the body member.

5. The introducer sheath assembly of claim 2, wherein the through hole in the body member is located at substantially the same axial position as the side port lumen such that the through hole, the side port lumen, the interior chamber of the side port member and the longitudinal channel of the body member remain in fluid communication as the side port member is rotated relative to the body member.

6. The introducer sheath assembly of claim 2, wherein the outer surface of the body member further includes a circumferential recess extending radially inwardly around the body member, and wherein the through hole is located within the circumferential recess.

7. The introducer sheath assembly of claim 6, wherein the outer surface of the body member further includes a first circumferential groove located proximal to the circumferential recess, and a second circumferential groove located distal to the circumferential recess, and wherein the hemostasis valve assembly further includes a first seal ring retained within the first circumferential groove and a second seal ring retained within the second circumferential groove, the first and second seal rings configured to seal against an interior surface of the side port member side wall.

8. The introducer sheath assembly of claim 1, wherein the side port member includes a proximal end face and a distal end face.

9. The introducer sheath assembly of claim 2, wherein the body member further includes a proximal end portion, and wherein the hemostasis valve assembly further includes an end cap secured to the proximal end portion of the body member, the end cap including the proximal opening of the hemostasis valve assembly.

10. The introducer sheath assembly of claim 9, wherein the proximal end portion of the body member further includes a radial flange abutting a proximal face of the side port member, and a circumferential notch located proximal to the radial flange, and wherein the end cap includes an inwardly extending circumferential tab that engages the circumferential notch to secure the end cap to the body member.

11. The introducer sheath assembly of claim 1, further comprising a handle assembly coupled to the sheath member.

12. An introducer sheath assembly comprising:
   a tubular sheath member having a proximal end portion including a proximal end, a distal end portion terminating in a distal tip, and an internal sheath lumen extending through the proximal and distal end portions of the sheath member;

a distal end fitting including a proximal face having an annular groove, and a distal end connected to the proximal end of the sheath member;

a body member including an outer surface and an inner surface defining a longitudinal channel, a portion of the body member disposed within the interior chamber of the side port member and including a lateral through hole extending through the outer and inner surfaces and fluidly coupling the longitudinal channel with the side port lumen and the interior chamber of the side port member, the body member including a distal annular lip configured to be received within the annular groove of the distal fitting to secure the body member to the distal fitting; and a hemostasis valve assembly including a distal end portion coupled to the proximal end of the sheath member, a proximal opening generally aligned with the sheath lumen to permit introduction of an instrument therethrough, a seal member positioned distal to the proximal opening to inhibit fluid leakage through the proximal opening, and a side port member between the seal member and the distal end portion of the hemostasis valve assembly, the side port member including:

a side wall having an inner surface defining an interior chamber in fluid communication with the sheath lumen; and a side port fitting extending laterally from the sidewall and including a side port lumen extending through the side wall in fluid communication with the interior chamber, wherein the side port member is configured to be axially rotatable relative to the sheath member and a handle assembly, and wherein the seal member is retained between the proximal end portion of the body member and the end cap, and wherein a proximal end portion of the body member includes an annular groove oriented toward the end cap, and wherein the seal member includes a proximal face and a distal face, and an annular lip extending axially from the distal face configured to be received in the annular groove of the body member.

13. A deflectable introducer sheath assembly comprising:

a tubular sheath member having a proximal end portion including a proximal end, a distal end portion terminating in a distal tip, and an internal sheath lumen extending through the proximal and distal end portions of the sheath member;

a handle assembly coupled to the proximal end portion of the sheath member;

a distal end fitting including a proximal face having an annular groove, and a distal end connected to the proximal end of the tubular sheath member;

a body member including a distal annular lip configured to be received within the annular groove of the distal fitting to secure the body member to the distal fitting; and a hemostasis valve assembly coupled to the proximal end of the sheath member and configured to permit introduction of an instrument into the sheath lumen while inhibiting fluid leakage from the introducer sheath assembly, the hemostasis valve assembly including a side port member including a side port fitting having a side port lumen in fluid communication with the sheath lumen, wherein the side port member is axially rotatable relative to the sheath member and the handle assembly.

14. The introducer sheath assembly of claim 13, wherein the side port member is tubular and includes a sidewall having an inner surface defining an interior chamber in fluid communication with the sheath lumen, and wherein the side port lumen extends through the side wall.

15. The introducer sheath assembly of claim 13, wherein the body member includes an outer surface and an inner surface defining a longitudinal channel, a portion of the body member disposed within the interior chamber of the side port member and including a lateral through hole extending through the outer and inner surfaces and fluidly coupling the longitudinal channel with the side port lumen and the interior chamber of the side port member.

16. The introducer sheath assembly of claim 15, wherein one or both of the side wall of the side port member and the body member are made of a substantially transparent material.

* * * * *